(12) United States Patent
Fuchs et al.

(10) Patent No.: US 8,195,476 B2
(45) Date of Patent: Jun. 5, 2012

(54) METHOD FOR THE ADMINISTRATION OF MEDICAL PATIENT DATA

(75) Inventors: Friedrich Fuchs, Roettenbach (DE); Rainer Kuth, Herzogenaurach (DE); Thorsten Opderbeck, Erlangen (DE); Sabine Schaeffer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 2261 days.

(21) Appl. No.: 10/425,092

(22) Filed: Apr. 29, 2003

(65) Prior Publication Data

US 2003/0229521 A1   Dec. 11, 2003

(30) Foreign Application Priority Data

Apr. 29, 2002 (DE) .................................. 102 19 098

(51) Int. Cl.
*G06Q 50/00* (2012.01)
(52) U.S. Cl. ................................. 705/2; 705/3
(58) Field of Classification Search .................. 705/51, 705/37, 2–4; 600/300, 316, 425, 407; 707/4, 707/10, 104.1
See application file for complete search history.

(56) References Cited

U.S. PATENT DOCUMENTS

| | | | | |
|---|---|---|---|---|
| 4,667,292 A | * | 5/1987 | Mohlenbrock et al. | 705/2 |
| 5,359,509 A | * | 10/1994 | Little et al. | 705/2 |
| 5,519,607 A | * | 5/1996 | Tawil | 705/2 |
| 6,140,936 A | | 10/2000 | Armstrong | |
| 6,463,417 B1 | * | 10/2002 | Schoenberg | 705/2 |
| 6,523,009 B1 | * | 2/2003 | Wilkins | 705/3 |
| 6,540,672 B1 | * | 4/2003 | Simonsen et al. | 600/300 |
| 6,656,114 B1 | * | 12/2003 | Poulsen et al. | 600/300 |
| 6,879,959 B1 | * | 4/2005 | Chapman et al. | 705/2 |
| 6,915,265 B1 | * | 7/2005 | Johnson | 705/2 |
| 7,016,856 B1 | * | 3/2006 | Wiggins | 705/2 |
| 7,213,009 B2 | * | 5/2007 | Pestotnik | 706/46 |
| 7,447,643 B1 | * | 11/2008 | Olson et al. | 705/2 |
| 2001/0041991 A1 | * | 11/2001 | Segal et al. | 705/3 |
| 2002/0010679 A1 | * | 1/2002 | Felsher | 705/51 |
| 2002/0029157 A1 | * | 3/2002 | Marchosky | 705/3 |

(Continued)

FOREIGN PATENT DOCUMENTS

WO    WO 00/32088    6/2000

(Continued)

OTHER PUBLICATIONS

JTEC Panel on Knowledge-Based Systems in Japan (May 1993).

(Continued)

*Primary Examiner* — Gerald J. O'Connor
*Assistant Examiner* — Natalie A Pass
(74) *Attorney, Agent, or Firm* — Schiff Hardin LLP

(57) ABSTRACT

In a method for the administration of medical patient data with a centralized or decentralized patient medical file having secured access enabled by the patient or an enable code administered by the patient, wherein the patient data contain all previous examinations with data representing when the examination was conducted and the findings, a check-in of a patient into the device is implemented before a new examination by the physician, the check-in ensuing upon indication of the initial suspicion as well as of the planned examinations, an enable of these examination via a comparison device, particularly an expert system, ensues only when no relevant, previous examinations are present in a specific, preceding time span, and invoicing for the new examination is possible only in conjunction with a documentation of the examination and its results in the patient medical file.

15 Claims, 1 Drawing Sheet

U.S. PATENT DOCUMENTS

| | | | |
|---|---|---|---|
| 2002/0133503 A1* | 9/2002 | Amar et al. | 707/104.1 |
| 2003/0060688 A1* | 3/2003 | Ciarniello et al. | 600/300 |
| 2003/0083903 A1* | 5/2003 | Myers | 705/2 |
| 2003/0187692 A1* | 10/2003 | Park | 705/2 |
| 2004/0172291 A1* | 9/2004 | Knowlton | 705/2 |

FOREIGN PATENT DOCUMENTS

| | | |
|---|---|---|
| WO | WO 02/29664 | 4/2002 |

OTHER PUBLICATIONS

Answers.com article "Expert System".
Definition from The Free Dictionary for "Expert System".
Printout from Decision Maker Website describing "Expert System".
Printout from Penn State University College of Agricultural Science Expert Systems Development Group.

* cited by examiner

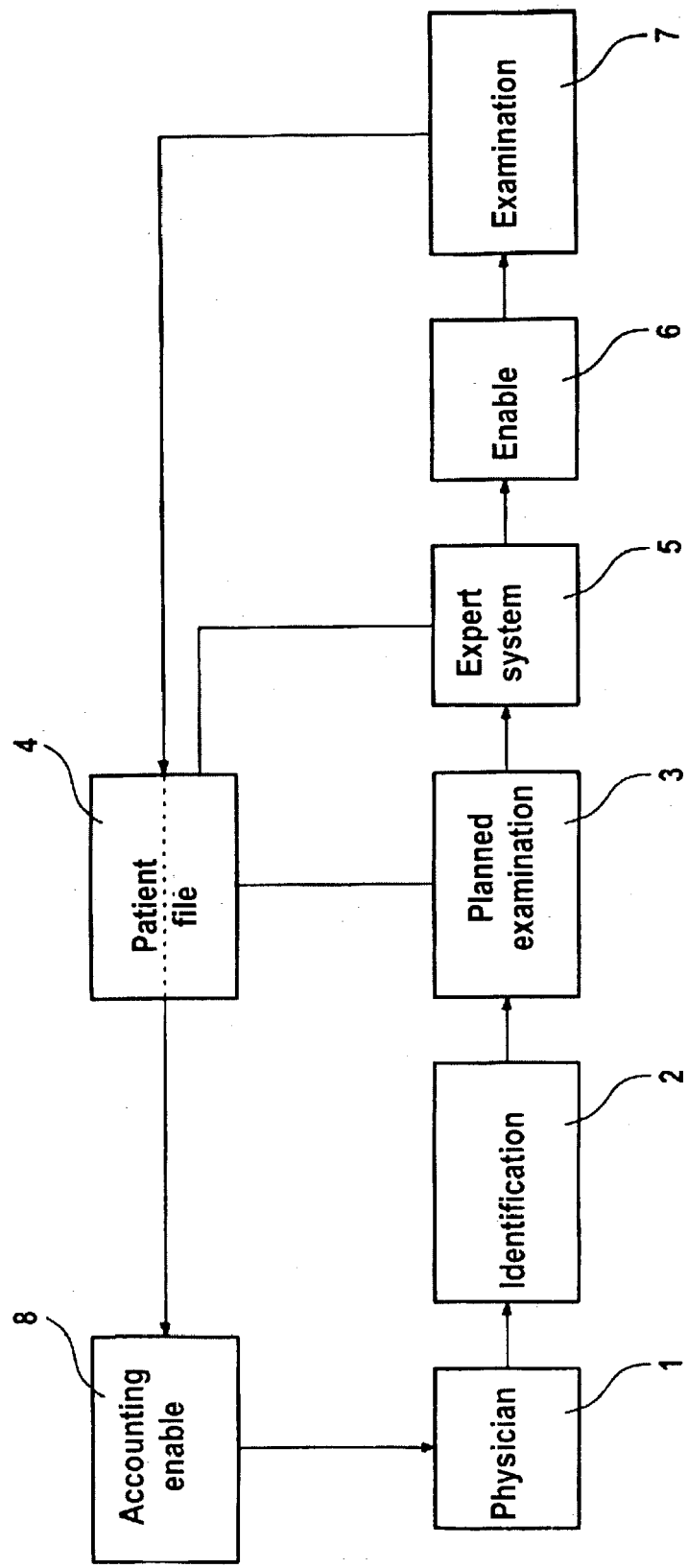

METHOD FOR THE ADMINISTRATION OF MEDICAL PATIENT DATA

BACKGROUND OF THE INVENTION

1. Field of the Invention

The present invention is directed to a method for the administration of medical patient data with a centralized or decentralized patient file having secured access enabled by the patient or an enable code administered by the patient, wherein the patient data contain all previous examinations with data representing when the examination was conducted as well as the findings, and wherein a check-in of a patient into the device is implemented before a new examination by the physician.

2. Description of the Prior Art

Many patients currently get multiple examinations on the basis of the same complaint because the results from previous diagnoses are not available to the currently attending physician. Particularly in the case of diagnoses involving the use of radiation, it is desirable to avoid multiple examinations in order to avoid unnecessary radiation stressing. In certain instances, for example children or expectant mothers, a certain minimum waiting time until the next examination can be required following an X-ray examination.

Another problem in the current medical system, which offers great freedom for the patients in selecting a physician, is so-called doctor hopping. Within a short time, patients go to doctors in the same discipline and they implement comparable multiple examinations.

Medical patient data administration systems are known such as German OS 199 01 438—wherein the physicians have access via an enable code administered by the patient to a centralized or decentralized patient file in which a large variety of previous examinations by other physicians in clinics or the like are stored. Although such a system enables a newly visited physician to have access to earlier examination results, it is not assured that this patient file is kept complete, i.e. whether all previous examinations are really entered, and whether unnecessary double examinations, specifically expensive apparatus examinations with X-ray devices, magnetic resonance tomography systems or the like, are still not prevented. As is known from experience, many medical practitioners would rather produce their own images in a re-examination of a patient that have recourse to examination results of earlier examinations.

SUMMARY OF THE INVENTION

An object of the present invention is to provide a medical data administration system of the type initially described wherein it is assured that all examinations are documented in the patient file and unnecessary duplicate examinations are avoided.

This object is achieved in accordance with the invention in a system of the type initially described wherein the check-in ensues upon indication of the initial suspicion necessitating an examination as well as the planned examinations, whereby an enable of this examination via a comparison device, particularly an expert system, ensues only if no relevant, previous examinations are present in a specific, preceding time span, and wherein invoicing the new examination is possible only in conjunction with a documentation of the examination and its results in the patient file.

The inventive patient data administration system assures that all previous examinations are in fact contained in the patient file because, namely, the examining physician or the examining clinic can implement an invoicing for these examinations with the health insurer or the patient only when the examination results have been documented in the patient file. This forces the physician to supplement the patient file. On the basis of such a patient file wherein all previous examinations are entered, a determination can be made with certainty as to whether a comparable, previous examination already exists within a certain time span preceding the new examination, by means of the expert system when a later examination is planned. The new examination thus is inhibited by the expert system. As used herein "inhibited" means that the physician—given implementation of the examination contrary to this inhibition—cannot bill the costs for the examination. Moreover, the physician may be liable to prosecution if, contrary to the instruction of the expert system, the physician carries out a highly stressful second examination of the patient within a short follow-up time.

Manipulations can be largely precluded by the accountability for a medical examination by the physician or in a clinic being established only when the examination and its results are documented in the patient file. Additionally in an embodiment of the invention the comparison results of the expert system as well as any enables or non-enables as have occurred are automatically entered into the patient file.

In addition to being patient files decentrally distributed among a number of servers, for example in the Internet, the inventive patient data administration system is especially suited for patient files stored in mobile fashion with the patient, whereby the patient file is stored, for example, on a digital, portable storage medium such as a writeable CD-ROM or DVD-ROM.

The access to the patient file can be secured in a known way via in insurance card and/or a fingertip sensor and/or an iris measurement sensor and/or a password or the like.

Before an examination, the patient checks in, with the patient identifying him/herself in an unambiguous manner. After entering the initial suspicion and the planned new examination, a check is then made to determine whether a relevant examination for the same condition or, respectively, for the same suspicion has been made, within a time frame that can differ dependent on the disease or suspicion. If this is the case, the accountability is precluded. At the same time, the currently attending physician has access to the previous examinations. This can be a right to read the mobile data storage of the patient or a right to read a data bank in the same hospital or a data bank that can be reached by modem or Internet. The read permission is achieved via the identification of the patient. Technologically, portable electronic devices with 5 Gbyte are currently available, for example from the Apple company. Other media are the aforementioned CD-ROMs or DVD-ROMs in what is referred to as multi-session operation, whereby new datasets can be added repeatedly to the data that are already stored.

If there are doubts about the quality of a pervious examination or in the appertaining finding, then a provisional enable of the accounting subject to reservation, is provided upon an indication of the grounds therefor. If it turns out in the examination or the following diagnosis that the prior examination was of inadequate quality, then a normal enable of the subsequent examination ensues for accounting. Optionally, the accounting for the previous examination can be revoked, or the physician or the clinic that produced the prior examination with deficient quality can be charged, for example, for the costs for the subsequent examination.

DESCRIPTION OF THE DRAWINGS

The single FIGURE is a block circuit diagram of the function and operating sequence of an inventive medical patient data administration system.

DESCRIPTION OF THE PREFERRED EMBODIMENTS

When checking a patient in at the physician's or in a clinic 1, an identification ensues with the assistance of a suitable access code in step 2, with which the suspected disease raised by the physician as well as the planned examinations are entered into the patient file 4. A comparison of the data in the patient file 4 to the planned examinations ensues in a comparison device, particularly an expert system. Dependent on the presence or absence of comparable examinations at the time of preceding the planned examination that is variable dependent on the illness, the expert system outputs an enable of the examinations 6, which is followed by a documentation 7 of the examination results. This documentation 7 must be entered into the patient file 4, in order for an enable of the accounting for the examination for the physician to ensue in step 8.

Regardless of the way in which the patient file is maintained, i.e. whether it is maintained on a card or some other storage with the patient, whether it is deposited in the centralized or decentralized data bank or is even deposited distributed in the Internet, the inventive embodiment of the patient data administration assures that the patient file is complete in all instances, since the physicians or clinics cannot bill their examinations otherwise. Unnecessary, multiple examinations are prevented by inhibiting the invoicing. Physicians likely will implement unnecessary, subsequent examinations—which currently are often implemented—if they know from the very outset that this examination cannot be billed. Not only is the radiation stress on the patient due to involved examination methods reduced by avoiding these unnecessary redundant examinations, but the costs to the health system are reduced. At the same time, the quality of medical examinations is enhanced since it is easier to perform a quality check. In general, thus, a cost reduction, a quality enhancement and better health management are achieved.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for administering medical patient data comprising the steps of:
    electronically storing medical data for a patient in a secured patient medical file with restricted access, said medical patient data containing data representing all previous examinations of the patient including a date of each examination and findings from each examination;
    before implementing a new examination of the patient with a medical device prescribed by a physician, requiring automatic electronic, non-manual comparison of said patient medical file to data representing said new examination to obtain an electronic comparison result;
    automatically electronically, non-manually preventing billing of costs of said new examination if said electronic comparison result indicates a previous examination exists comparable to said new examination in said patient medical file within a predetermined time span preceding the comparison; and
    when said new examination is implemented, automatically determining if data representing a documentation of said new examination have been entered in said patient file, and automatically electronically, non-manually preventing monetarily charging said patient for a cost associated with said new examination if said data representing a documentation of said new examination are not entered in said patient medical file.

2. A method as claimed in claim 1 comprising employing a centralized file as said patient medical file.

3. A method as claimed in claim 1 comprising employing a decentralized file as said medical patient medical file.

4. A method as claimed in claim 1 comprising comparing said patient medical file to said data representing said new examination at a time said new examination is planned by said physician.

5. A method as claimed in claim 1 comprising restricting access to said patient medical file by enabling access to said patient medical file only by said patient.

6. A method as claimed in claim 5 comprising enabling access to said patient medical file by said patient by requiring entry of an enable code administered by said patient.

7. A method as claimed in claim 1 comprising said patient medical file in a medium adapted to be carried by said patient.

8. A method as claimed in claim 7 comprising storing said patient medical file in a digital portable storage medium.

9. A method as claimed in claim 8 comprising storing said patient medical file on a medium selected from the group consisting of a writeable CD ROM and a DVD ROM.

10. A method as claimed in claim 1 comprising conducting said comparison using an expert system.

11. A method as claimed in claim 1 comprising entering said comparison result in said patient medical file.

12. A method as claimed in claim 1 comprising restricting access to said patient medical file using an insurance card.

13. A method as claimed in claim 1 comprising restricting access to said patient medical file using a fingerprint sensor.

14. A method as claimed in claim 1 comprising restricting access to said patient medical file using an iris measurement sensor.

15. A method as claimed in claim 1 comprising restricting access to said patient medical file using a password.

* * * * *